US00PP09285P

United States Patent [19]

Machin

[11] Patent Number: Plant 9,285

[45] Date of Patent: Sep. 12, 1995

[54] CHRYSANTHEMUM PLANT NAMED 'ENAMOUR'

[75] Inventor: Barrie J. Machin, Hants, England

[73] Assignee: Goldstock Breeding Limited, Hants, England

[21] Appl. No.: 254,265

[22] Filed: Jun. 3, 1994

[51] Int. Cl.[6] ..... A01H 5/00
[52] U.S. Cl. ..... Plt./82.4
[58] Field of Search ..... Plt. 82.4, 74.1

[56] References Cited

U.S. PATENT DOCUMENTS

P.P. 4,286 8/1978 Jessel, Jr. et al. ..... Plt./82.4
P.P. 6,934 7/1989 Van der Knaap ..... Plt./82.4

*Primary Examiner*—Howard J. Locker
*Attorney, Agent, or Firm*—Foley & Lardner

[57] ABSTRACT

A new Chrysanthemum cultivar named Enamour, characterized by the combined features of cup-shaped capitulum form, daisy capitulum type, pink floret color, capitulum diameter of 5–6 cm, a response period of 49–52 days when grown with 14 long days prior to start of short days, and a plant height of 110 cm.

3 Drawing Sheets

The present invention comprises a new and distinct cultivar of Chrysanthemum, botanically known as *Dendranthema grandiflora* and referred to by the cultivar name Enamour.

Enamour was originated from a cross made by the inventor Barrie J. Machin in a controlled breeding program in Fareham, England in 1987. The female parent of Enamour was a seedling known as Framint, an unpatented cultivar described as a cut spray single daisy type having white ray florets, a diameter of capitulum of 4 cm to 5 cm when fully open, a flowering response to short days of 51–53 days, a plant height of 100 cm when grown with 14 long days prior to start of short days, a peduncle length of the first lateral of 9 cm and of the fourth lateral of 11 cm, and a columnar spray formation. The above characteristics are based on plants grown in Fareham, England.

The male parent of Enamour was a seedling identified as Pink Moon, an unpatented cultivar described as a daisy type having pale pink ray florets, diameter of capitulum of 6 cm, a flowering response of 56 days, a plant height of 110 cm when grown with 14 long days prior to start of short days, a peduncle length of the first lateral of 8 cm and of the fourth lateral of 11 cm, and a columnar spray formation. The above characteristics are similarly based on plants grown in Fareham, England.

Enamour was discovered and selected as one flowering plant within the progeny of the stated cross by Barrie Machin in Oct. 1988 in a controlled environment in Fareham England.

The first act of asexual reproduction of Enamour was accomplished when vegetative cuttings were taken from the initial selection in Jan. 1989 in a controlled environment in Fareham, England by Barrie J. Machin.

Horticultural examinations of controlled flowerings of successive plantings has shown that the unique combination of characteristics as herein disclosed for Enamour are firmly fixed and are retained through successive generations of asexual reproduction.

Enamour has not been observed under all possible environmental conditions. The phenotype may vary somewhat with variations in environment such as temperature, light intensity and day length, without, however, any variance in genotype.

The following observations, measurements and comparisons describe plants grown in Fareham, England under greenhouse conditions which approximate those generally used in commercial greenhouse practice.

The following traits have been repeatedly observed and are determined to be basic characteristics of Enamour which in combination distinguish this Chrysanthemum as a new and distinct cultivar.

1. Cup-shaped capitulum form which does not flatten with maturity.
2. Daisy capitulum type.
3. Pink ray floret color.
4. Diameter across face of capitulum of 5–6 cm when fully open, with a disc diameter of 1.5 cm.
5. Flowering response under normal temperatures is 49 to 52 days after start of short days.
6. Peduncle length of the first lateral at flowering after removal of the apical bud and without growth regulator applications is 11 cm; peduncle length of the fourth lateral at flowering is 13 cm.
7. Plant height of 110 cm.

The accompanying photographic drawings show typical inflorescence and leaf characteristics of Enamour, with the colors being as nearly true as possible with illustrations of this type.

The photograph on sheet 1 is a color photograph of Enamour grown as a spray cut mum in Fareham, England.

The black and white photo on sheet 2 shows three views of typical mature flowers of Enamour, and the photo on sheet 3 illustrates the top surface and under surfaces of leaves of Enamour at three stages of growth.

Of the commercial cultivars known to the inventor, the most similar in comparison to Enamour is the cultivar Camino Pink, disclosed in U.S. Plant Pat. No. 4,286. Reference is made to the attached chart A which compares certain characteristics of Enamour with the same characteristics of Camino Pink. Similar traits are capitulum type and diameter, response and spray formation. Although the ray floret color of both cultivars is generally described as pink, Enamour has a darker pink color. In addition, the flowers of Enamour are cup-shaped in form compared to the flat form of Camino Pink, and Enamour is somewhat taller with longer peduncles.

In the following description color references are made to The Royal Horticultural Society Color chart. The color values were determined on plant material grown as a single spray cut mum in Fareham, England in 1989.

Classification:

*Botanical.*—*Dendranthema grandiflora* cv Enamour.

*Commercial.*—Daisy spray cut mum.

Inflorescence

A. Capitulum:

*Form.*—Cup-shaped.

*Type.*—Daisy.

*Diameter across face.*—5–6 cm.

B. Corolla of ray florets:

*Color (generally).*—Pink.

*Color (upper surface).*—RHS 65C.

*Color (under surface).*—RHS 65D.

*Shape.*—Long, pointed and flat.

C. Corolla of disc florets:

*Color (mature).*—13A.

*Color (immature).*—143C.

*Diameter.*—Approximately 15 mm.

D. Reproductive organs:

*Androecium.*—Present only in disc florets; no pollen found.

*Gynoecium.*—Present in both disc and ray florets.

Plant

A. General appearance:

*Height.*—110 cm.

*Branching pattern.*—Regular branching habit, typically one branch developing per leaf axil.

B. Foliage:

*Color (upper surface).*—147A.

*Color (under surface).*—147B.

*Shape.*—Pinnately lobed with widely spaced indentations in margin; see photograph. ps

CHART A

| CHARACTERISTICS | ENAMOUR | CAMINO PINK |
|---|---|---|
| Ray floret color | pink | pale pink |
| Capitulum form and type | cup-shaped daisy | flat daisy |
| Diameter across face of capitulum | 5–6 cm | 5.5–6.5 cm |
| Flowering response | 49–52 days | 49–52 days |
| Plant height | 110 cm | 100 cm |
| Peduncle length | | |
| 1st lateral | 11 cm | 7 cm |
| 4th lateral | 13 cm | 9 cm |
| Spray formation | columnar | columnar |

It is claimed:

1. A new and distinct Chrysanthemum plant named Enamour, as described and illustrated.

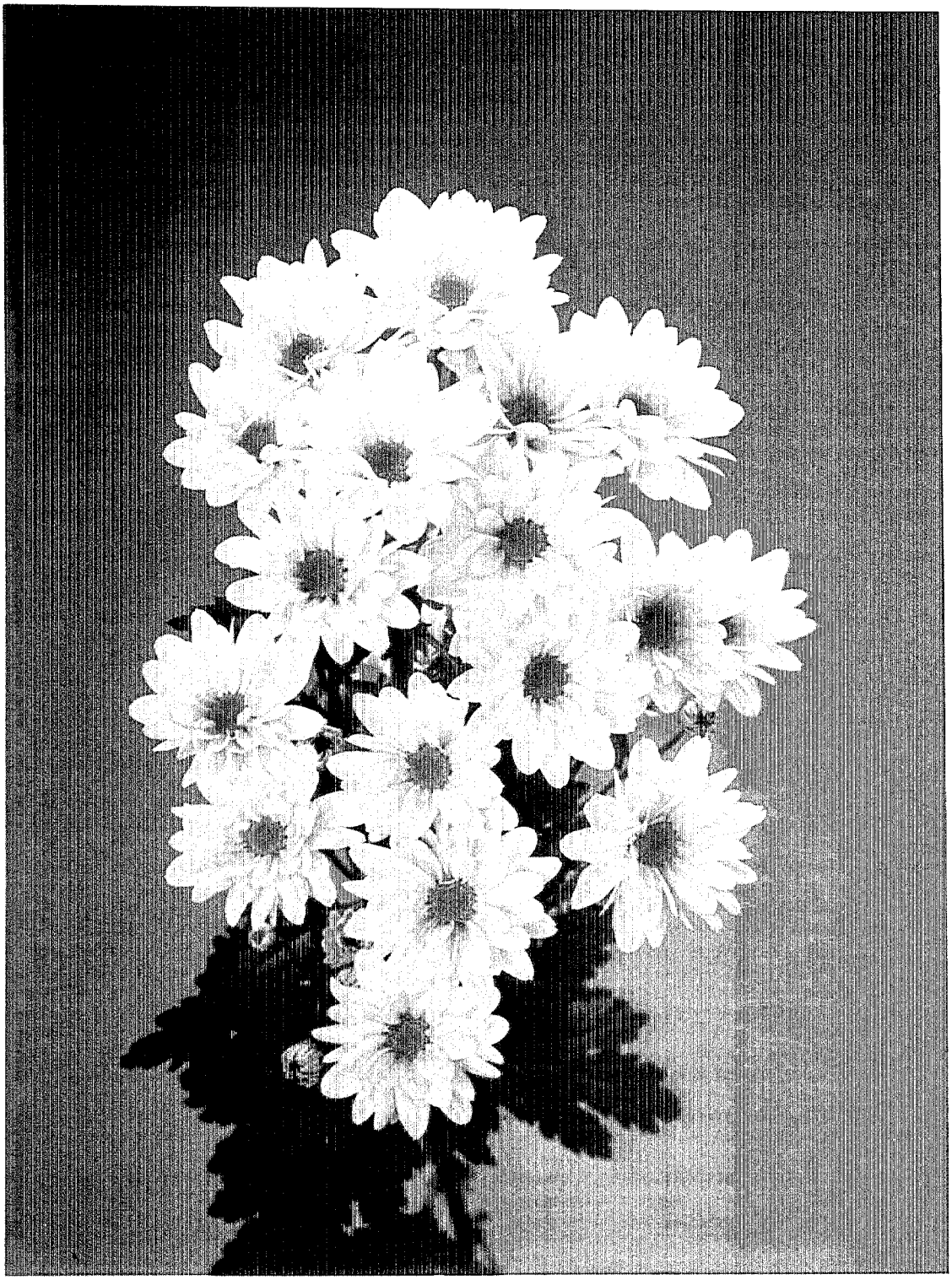

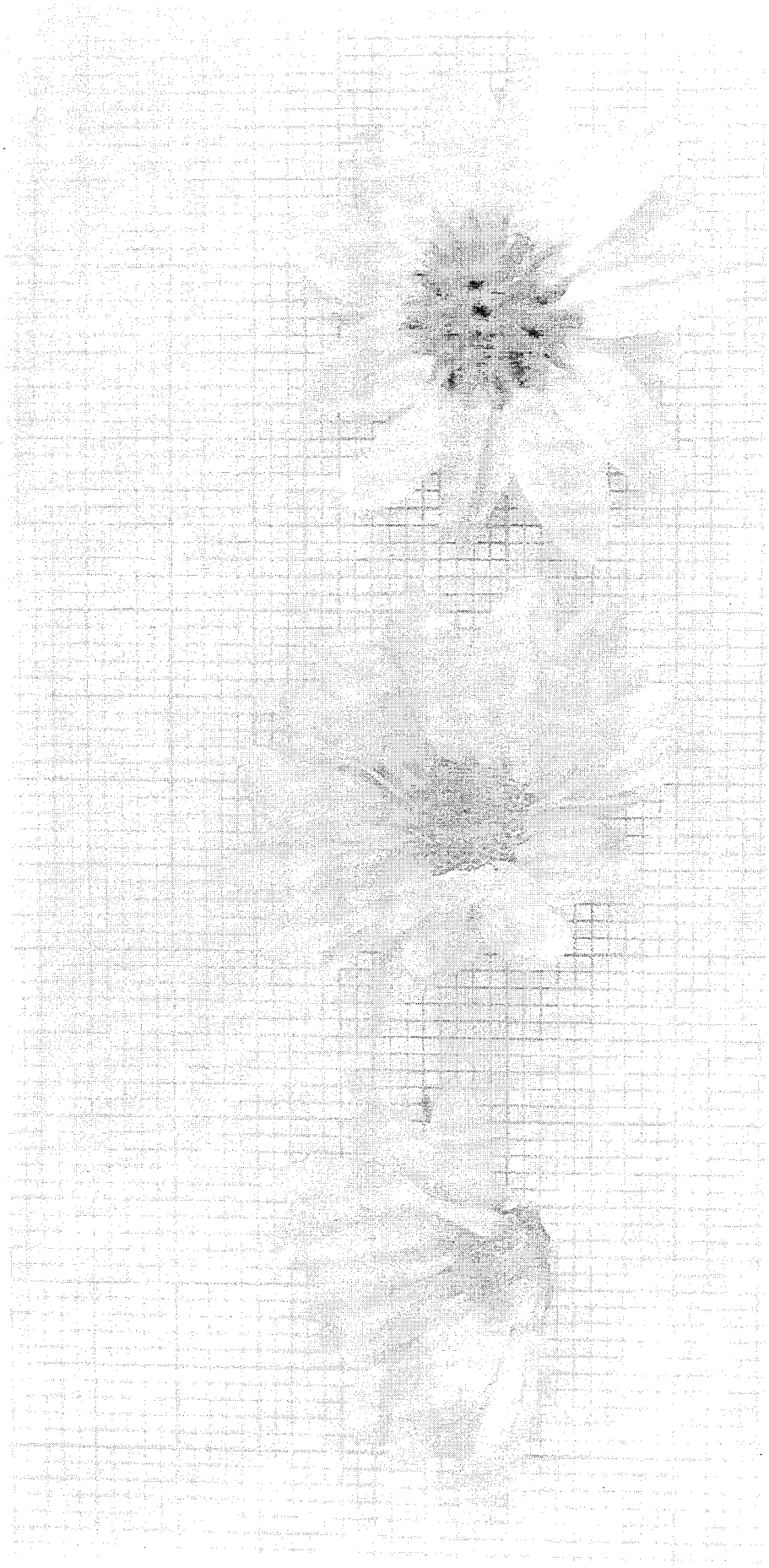

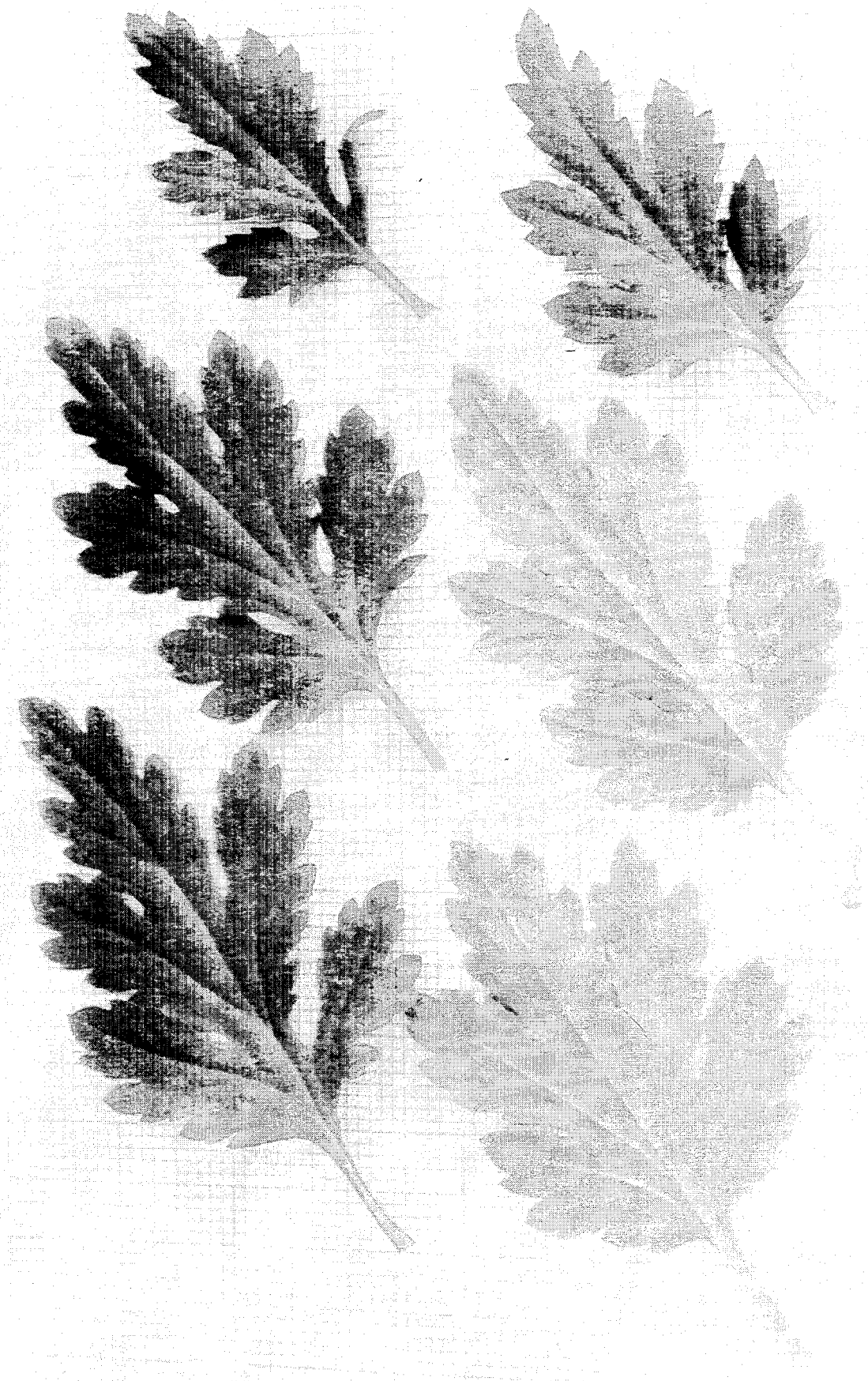

* * * * *